ps patent

United States Patent [19]
Schneider et al.

[11] 4,064,180
[45] Dec. 20, 1977

[54] ALKYL ETHERS OF BINOR-S

[75] Inventors: Abraham Schneider, Overbrook Hills; Edward J. Janoski, Havertown, both of Pa.

[73] Assignee: Sun Ventures, Inc., St. Davids, Pa.

[21] Appl. No.: 578,308

[22] Filed: May 16, 1975

[51] Int. Cl.² .............................................. C07C 43/18
[52] U.S. Cl. .................................. 260/611 F; 44/78; 149/120; 149/109.4
[58] Field of Search ...................................... 260/611 F

[56] References Cited
PUBLICATIONS

Paquette et al., J.A.C.S. 94, (1972), pp. 5096–5098.

Monick, Alcohols, (1968), 93, 94, 150–152.

Primary Examiner—Bernard Helfin
Attorney, Agent, or Firm—J. Edward Hess; Donald R. Johnson; Anthony Potts, Jr.

[57] ABSTRACT

Ionic alcoholysis of Binor-S, a $C_{14}$ heptacyclic, saturated hydrocarbon, in the presence of a primary alcohol and hydrogen, yields a low melting point product containing novel alkyl ethers of Binor-S. Alcoholysis occurs at about 50°–300° C. and at about 100–10,000 p.s.i.g. in the presence of Raney nickel, palladium-on-carbon or palladium-on-alumina catalyst promoted by a hydrogen halide or its equivalent. Resulting product has utility as a high energy fuel.

24 Claims, No Drawings

ALKYL ETHERS OF BINOR-S

CROSS REFERENCE TO RELATED APPLICATION

This application is related to U.S. application Ser. No. 578,070, filed same date by same inventors. Subject matter of this related application is the hydrogenolysis of Binor-S.

BACKGROUND OF THE INVENTION

The invention herein described was made in the course of or under a contract thereunder with the United States Air Force Systems Command.

This invention relates to mixtures of alkyl ethers of Binor-S resulting from the alcoholysis of Binor-S in the presence of primary alcohols during the hydrogenolysis of Binor-S. More particularly, the invention relates to mixtures of hexacyclic alkyl ethers resulting from the alcoholysis of Binor-S, a $C_{14}$ heptacyclic saturated hydrocarbon during hydrogenolysis of Binor-S in the presence of primary alcohols and promoting amounts of hydrogen halide or its equivalent.

It is an object of present invention to provide novel composition of alkyl ethers of hexacyclics which composition is characterized by a low freezing point, a low melting point and by favorable net volumetric heat of combustion. Said composition has utility as a high energy fuel which can be used in either jet or rocket propulsion. Jet propulsion includes a jet engine which can be used for a missile or a plane or other devices and includes the three basic types, i.e., ramjet, turbo-jet and pulse jet. The term jet generally refers to a device requiring air whereas rocket generally refers to a device containing its own oxygen.

It is an object to also provide novel compositions wherein the compositions are essentially alkyl ethers of hexacyclics.

It is also an object of present invention to provide a novel method for preparing the foregoing novel compositions.

Preparation of Binor-S is disclosed in Journal of the American Chemical Society; 88:21, Nov. 5, 1966, pages 4890–4894, title of Article "π Complex Multicenter Reactions Promoted by Binuclear Catalyst Systems." "Binor-S", a New Heptacyclotetradecane via Stereospecific Dimerization of Bicycloheptadiene", by G. N. Schrauzer, B. N. Bastian and G. A. Fosselius. Binor-S is known by its chemical name of endo, cis, endoheptacyclo[5.3.1.1$^{2,6}$.1$^{4,12}$.1$^{9,11}$0$^{3,6}$.0$^{8,10}$]tetradecane. Its melting point is about 65° C. Binor-S can be depicted by the following structural formula:

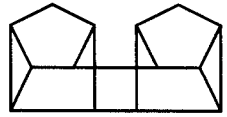

Binor-S is a $C_{14}H_{16}$ hydrocarbon containing seven rings and a C/H atomic ratio of 0.875.

Preparation of dimers of bicycloheptadiene is disclosed in U.S. Pat. No. 3,326,993, issued June 20, 1967. The latter disclosed that a mixture of bicycloheptadiene dimers has utility as high energy fuel.

Hydrogenation of the foregoing bicycloheptadiene dimers improves its stability towards autoxidation, thereby enhancing its utility as a fuel. Such hydrogenated dimers of bicycloheptadiene, in which crystallization has been produced by maintaining at −110° F. (−78.9° C) are completely melted only by warming to +25° F. (−3.9° C). The rather high melting point of the last crystalline material of said dimer can hinder its fluid flow at low ambient temperatures.

In contrast applicant's entire product has a pour point of −75° F. (−59.3° C), a density of 1.0987 and a net volumetric heat of combustion of 159,600 BTU per gallon.

SUMMARY OF THE INVENTION

Binor-S is alcoholyzed in the presence of hydrogen using Raney nickel, palladium-on-carbon or palladium-on-alumina catalyst promoted by a hydrogen halide or its equivalent. Temperature of the alcoholysis is about 50°–300° C and the pressure is about 100–10,000 psig. A primary alcohol can serve as a solvent and reactant. Resulting product contains, in addition to any unreacted Binor-S, hexacyclic alkyl ethers of Binor-S, and others.

DESCRIPTION

The method of alcoholysis of Binor-S includes the presence of a promoter containing halide. The promoter can be a hydrogen-halide itself, e.g., hydrogen bromide or it can be from an organic halide such as ethyl chloride, isopropyl iodide, n-amyl bromide, ethylidene bromide, fluorobenzene, p-chlorotoluene, cyclopentyl chloride and the like. Alkyl halides, such as cyclohexylbromide are preferred. An alkyl halide is favored because an alkylhalide is more easily handled than the corresponding hydrogen halide. Of the four halides, i.e., fluoride, chloride, bromide and iodide, bromide is preferred. When an alkylhalide is used cyclohexylbromide, t-butyl chloride, isopropyl bromide and isopropyl chloride are preferred. In the presence of hydrogen the Raney nickel, palladium-on-carbon catalyst (hereinafter Pd/C), or palladium-on-alumina (hereinafter Pd/a) cause the alkylhalide to form the corresponding saturated alkyl hydrocarbon and the halide acid.

The amount of promoter containing halide present should be a promoting amount. While higher amounts accelerate reaction rates, too much could be uneconomical. An operative range is about 0.0001 to .004 gram moles of equivalent hydrogen halide per gram of Binor-S, a preferred range is about 0.0002 to 0.002. Equivalent hydrogen halide means either the amount of hydrogen halide used or that formed by the complete liberation of hydrogen halide from the organic halide.

The alcoholysis catalyst can be Raney nickel, Pd/C, or Pd/a. Normally the Pd/C contains about 0.5–12 weight percent palladium with a higher percentage, e.g., 10% preferred. Generally the amount of the catalyst present in that amount which is effective to catalyze the reaction. Typical operative ranges include about 0.1–10.0 weight percent based on the amount of Binor-S to be treated; a more operative range is about 0.5–5.0 weight percent.

The hydrogen used is free of sulfur or sulfur containing compounds. Any other impurity in the hydrogen which adversely affects the reaction, catalyst or products cannot be present.

The primary alcohol is a reactant but is also can serve as a solvent. As a solvent it reduces the viscosity of the Binor-S while it is undergoing alcoholysis. As a reactant it is the source of the R—CH$_2$—O— which contribute to the production of the ether. A primary alcohol is one which has a general structure R—CH$_2$OH wherein R is an alkyl or a hydrogen. As used herein "alkyl" refers to C$_n$H$_{2n}$+1. The number of carbon atoms in the alkyl may be as many as twenty; however, it is preferred that the alkyl contain no more than ten carbon atoms. A preferred alkyl is a paraffinic alkyl. The amount of alcohol present can vary to a trace whereby the amount of ether formed is also a trace amount to an amount in substantial excess of that necessary to react with all the Binor-S. An operative amount of alcohol would vary between about 1 to 1000 mole percent based on the moles of Binor-S; a more operative amount would be about 10 to 500.

Examples of the foregoing monohydric alcohols are methyl, ethyl, n-amyl, n-decyl, cetyl and stearyl.

The temperature of the alcoholysis generally will be between about 50°–300° C with 75°–250° C a preferred temperature range. The pressure of alcoholysis generally will be about 100–10,000 psig with 250–5000 psig a preferred pressure range.

The ionic alcoholysis of the Binor-S can be represented by the following formula reaction:

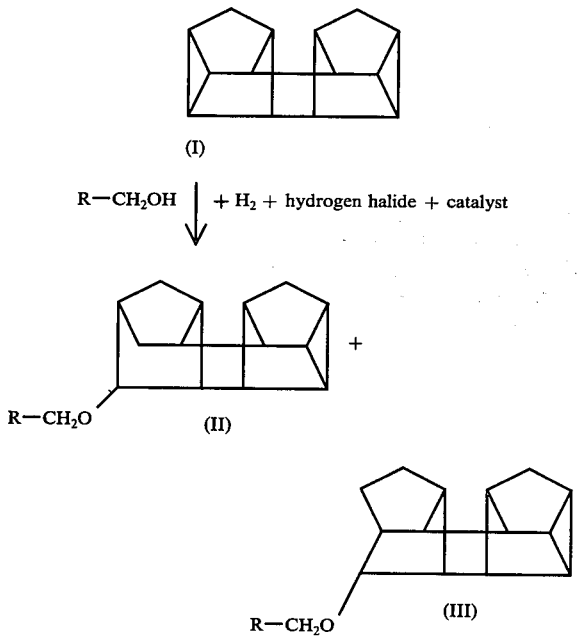

Compounds II and III accumulate with time and surprisingly further alcoholysis does not seem to occur. It appears that the monofunctional hexacyclic ether is resistant to further attack by a hydrogen halide.

The resulting mixture of present invention can contain unreacted I as well as ethers II and III. Other hydrocarbons can be present. The amount of ethers II and III present depend upon reaction times and the amount of alcohol present and other such variables. However, a mixture containing at least 30 weight % of the ethers can be used as a high energy fuel, mixture containing at least 40% is preferred while one containing at least 50% is more preferred.

Binor-S may be made by the dimerization of norbornadiene with the catalyst system CoBr$_2$(triphenylphosphine)$_2$-boron trifluoride etherate. Thus Binor-S, as prepared, may contain a trace amount of indigenous halide. This amount of indigenous halide may be sufficient to cause ionic alcoholysis. Binor-S which is carefully treated to remove any indigenous halide would have to have a halide added to it.

As noted heretofore the resulting mixture prepared by ionic alcoholysis of Binor-S has physical properties such as viscosity, density and heating value which enable it to be used as a high energy fuel. High energy fuel refers to a fuel that is used in volume-limited applications and therefore should contain a relatively large amount of BTU's per gallon. Such fuels are highly desirable in certain type jet propulsion such as missiles. Such fuels may also have application in volume-limited rockets. The foregoing devices are used in airplanes, boats, missiles, space vehicles and weapons and the like. In all these uses the ambient temperature can vary from a high 120° F (49° C) of a desert to the below freezing temperature of space or an arctic region.

Influencing the melting point of applicants' resulting mixture is the amount of unreacted high melting Binor-S contained therein. As the required melting point decreases the amount of unreacted Binor-S that can be present decreases. Unwanted and unreacted Binor-S can be removed by fractional crystallization, for example, or other known techniques. Also the amount of unreacted Binor-S remaining can depend on whether or not the fuel is heated to avoid fluid flow problems caused by ambient freezing temperatures.

The following examples serve to further illustrate applicants' invention; also describes how the starting material, i.e., Binor-S was prepared.

EXAMPLES

Preparation of Binor-S

Norbornadiene (bicyclo[2.2.1]hepta-2,5-diene) was dimerized with the catalyst system CoBr$_2$-(triphenylphosphine)$_2$-boron trifluoride etherate. The structure of the diene is as follows:

Afterwards methylene chloride was used to dissolve the organic phase of the reaction mixture and to separate the latter from the inorganic phase of catalyst components. Then the methylene chloride solution was washed with potassium carbonate to neutralize any free halogen acid and dried with the use of a drying agent such as anhydrous sodium sulfate. Upon cooling the treated methylene chloride solution Binor-S crystallized. The crystals were filtered from the liquid and then vacuum distilled to give solid Binor-S which had a grayish tinge. The foregoing procedure has been described in the literature. This procedure yields a Binor-S containing a trace amount of indigenous halide.

To prepare a "pure" Binor-S the mixture resulting from the dimerization of norbornadiene was dissolved in pentane. The resulting solution was washed with aqueous potassium carbonate and then dried as above. Upon cooling the Binor-S crystallized. The filtered crystals were vacuum distilled and the distilled Binor-S was recrystallized from acetone and redistilled under vacuum. The resulting "purified" Binor-S was colorless in contrast to the grayish tinged Binor-S containing the indigenous halide.

Alcoholysis of Binor-S

The following run was conducted at temperatures within 150°-230° C. and at pressures within 200-2700 psig in a high pressure, rocking type reactor of 0.3 liter capacity. Other operating information is given on the bottom of the accompanying Table. During the methanolysis, periodic monitoring of the contents of the reaction was carried out by withdrawing small samples from the liquid phase through a vent tube in the reactor. The samples were analyzed by high-efficiency capillary vapor phase chromatography with electronic integration of the data.

Results of methanolysis of the Binor-S are shown in the accompanying table. The data indicates that while small amounts of alkyl ethers of Binor-S were formed at 150° C. the amount is increased at a higher temperature of 200° C. After 40 hours the product mixture contained 48.7% of alkyl ethers of Binor-S. However, 3.75 hours later the amount of ether decreased. It is believed that this decrease does not reflect a change in composition but rather reflects the reproducibility of the particular instrument used for analysis.

Reflecting this question of reproducibility is the fact that the same product, i.e., the one after 43.75 hours, was analyzed on another vapor phase chromatography instrument. The results on this instrument are as follows: d13% Binor-S, 5% pentacyclics, 47% hexacyclics and 34% ether. The entire product had a pour point of −75° F., a density of 1.0987 and a net volumetric heat of combustion of 159,600 BTU/gallon.

Infrared, mass and NMR (nuclear magnetic resonance) studies confirmed that the ether is a methoxy substituted hexacyclic material with an intact cyclopropane ring and with the ether group attached to a secondary carbon rather than to a bridgehead position.

Analogous results will be obtained when the alcohol is ethyl, propyl, n-butyl, isobutyl, n-amyl, n-decyl, cetyl and stearyl. Also equivalent results will be obtained when Pd/C or Pd/a is used.

TABLE

| METHANOLYSIS OF BINOR-S WITH RANEY NICKEL | | | | |
|---|---|---|---|---|
| Reaction Time,* hrs. | 19.5 | 22 | 40 | 43.75 |
| Temperature, °C | 150 | 200 | 200 | 230 |
| Pressure, psig | 2000 | 2000 | 2000 | 2700 |
| Product, %+ | | | | |
| Binor-S | — | — | 16.7 | 15.8 |
| Ethers of Binor-S | small | increase | 48.7 | 43.3 |
| Hexacyclics | none | — | 30.0 | 36.7 |
| Unknowns | none | none | 5.2 | 4.2 |
| TOTAL | | | 100.6 | 100.0 |

*10.6 grams of crude Binor-S, 100 milliliters of methanol, 0.4 grams of Raney nickel; "crude" indicates that Binor-S contains indigenous halide.
+% are areas based on curves from vapor phase chromatography.

The invention claimed is:

1. A method for preparing a mixture containing alkyl ethers of Binor-S comprising:
   contacting Binor-S with hydrogen in the presence of a promoting amount of a promoter containing halide, an effective amount of a catalyst selected from the following group: palladium-on-carbon, palladium-on-alumina and Raney nickel; and a primary alcohol having the structure R—CH$_2$OH wherein R is hydrogen or a paraffinic alkyl containing C$_1$—C$_{10}$ atoms, said contacting occurring at a temperature of about 50°-300° C and at a pressure of about 100-10,000 p.s.i.g.; and
   whereby the melting point of the resulting mixture containing alkyl ethers of Binor-S enables said mixture to be used as a high energy fuel.

2. Method according to claim 1 wherein the contacting temperature is about 75°-275° C.

3. Method according to claim 2 wherein the contacting pressure is about 250-5000 p.s.i.g.

4. Method according to claim 1 wherein the contacting temperature is about 75°-275° C and the contacting pressure is about 250-5000 p.s.i.g.

5. Method according to claim 1 wherein the amount of promoter containing halide present is about 0.001-0.004 gram moles of equivalent hydrogen halide per gram of Binor-S.

6. Method according to claim 5 wherein the promoter is an organic halide.

7. Method according to claim 5 wherein the promoter is a hydrogen halide.

8. Method according to claim 5 wherein the amount of catalyst present is about 0.1-10 weight percent based on the amount of Binor-S.

9. Method according to claim 1 wherein the amount of alcohol present is about 1 to 1000 mole percent based on the mole of Binor-S.

10. Method according to claim 1 wherein the melting point enables the resulting mixture to be used in jet or rocket propulsion.

11. Method according to claim 10 wherein the amount of promoter containing halide present is about 0.0001-0.004 gram moles of equivalent hydrogen halide per gram of Binor-S; the catalyst present is in the amount of about 0.1-10 weight percent and the R of the primary alcohol contains C$_1$-C$_{10}$ atoms or is a hydrogen.

12. Method according to claim 11 wherein the primary alcohol is methanol and is present in the amount of about 10 to 500%.

13. Method according to claim 11 wherein the promoter is an organic halide.

14. Method according to claim 11 wherein the promoter is a hydrogen halide.

15. Method according to claim 12 wherein the promoter is an organic halide.

16. Method according to claim 12 wherein the promoter is a hydrogen halide.

17. Alkyl ethers of Binor-S having the following structures:

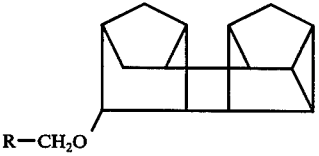

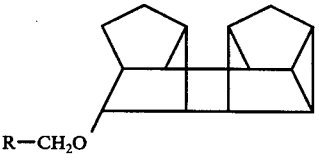

wherein R is a hydrogen or a paraffinc alkyl containing C$_1$-C$_{10}$ atoms.

18. Composition according to claim 17 wherein R is a paraffinic alkyl.

19. Composition according to claim 18 wherein the paraffinic alkyl is methyl.

20. A composition useful as a high energy fuel comprising a low melting mixture of alkyl ethers of Binor-S having the following structures:

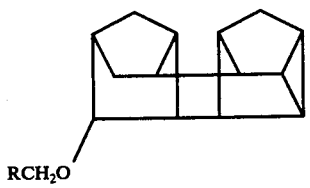

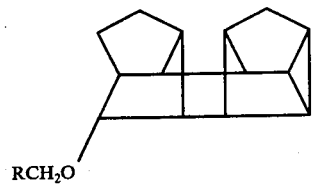

wherein R is a hydrogen or a paraffinic alkyl containing $C_1$-$C_{10}$ atoms and said mixture contains at least 30 weight % of said ethers, and said mixture is prepared by contacting Binor-S with a primary paraffinic alcohol in the presence of hydrogen and a catalyst.

21. Composition according to claim 20 wherein the paraffinic alkyl is methyl.

22. Composition according to claim 20 wherein the mixture contains at least 40% of said ether.

23. Composition according to claim 22 wherein the paraffinic alkyl is methyl.

24. Composition according to claim 23 wherein the mixture contains at least 50% of said ether.